United States Patent
Soodak

Patent Number: 5,458,730
Date of Patent: Oct. 17, 1995

[54] PEEL PACKAGE SEALING MACHINE

[75] Inventor: Charles I. Soodak, Silver Spring, Md.

[73] Assignee: American Fluoroseal Corporation, Silver Spring, Md.

[21] Appl. No.: 54,206

[22] Filed: Apr. 30, 1993

Related U.S. Application Data

[63] Continuation-in-part of Ser. No. 929,205, Aug. 14, 1992, Pat. No. 5,253,754.

[51] Int. Cl.$^6$ ........................ B32B 31/00
[52] U.S. Cl. ............ 156/579; 156/583.3; 156/583.8; 100/93 P
[58] Field of Search ........... 156/579, 581, 156/583.1, 583.3, 583.8; 219/243; 100/93 P; 425/394, DIG. 201

[56] References Cited

U.S. PATENT DOCUMENTS

| | | | |
|---|---|---|---|
| 1,139,069 | 5/1915 | Pfanstiehl | 156/579 |
| 2,390,550 | 12/1945 | Moore | 156/581 |
| 2,401,991 | 6/1946 | Walton et al. | 156/358 |
| 2,441,817 | 5/1948 | Huff | 156/579 |
| 2,535,171 | 12/1950 | Sundstrom | 156/289 |
| 2,589,756 | 3/1952 | Waters | 100/93 P |
| 2,615,113 | 10/1952 | Frye | 100/93 RP |
| 2,698,273 | 12/1954 | Miner et al. | 156/282 |
| 2,711,469 | 6/1955 | Southam et al. | 100/93 R |
| 2,712,343 | 7/1955 | Stanton | 156/583.3 |
| 2,743,761 | 5/1956 | Snyder et al. | 156/583.3 |
| 2,888,792 | 6/1959 | James | 53/79 |
| 3,035,381 | 5/1962 | Hosso | 53/568 |
| 3,149,015 | 9/1964 | Lindsay | 156/502 |
| 3,269,885 | 8/1966 | Cianci | 156/583.3 |
| 3,272,674 | 9/1966 | Sachs et al. | 156/282 |
| 3,322,603 | 5/1967 | Grasso | 156/579 |
| 3,412,233 | 11/1968 | Wilkie | 219/230 |
| 3,551,952 | 1/1971 | Morse | 100/93 P |
| 3,597,587 | 8/1971 | Baum | 219/243 |
| 3,614,383 | 10/1971 | Watts | 219/243 |
| 3,624,348 | 11/1971 | Berset | 219/243 |
| 3,624,349 | 11/1971 | Mayer | 219/243 |
| 3,752,725 | 8/1973 | Freeman | 156/367 |
| 3,822,164 | 7/1974 | Guido et al. | 156/358 |
| 3,830,681 | 8/1974 | Wilson | 156/583.3 X |
| 3,847,712 | 11/1974 | Hubbard | 156/515 |
| 3,867,226 | 2/1975 | Guido et al. | 156/229 |
| 3,895,214 | 7/1975 | Winter | 219/230 |
| 4,016,021 | 4/1977 | La Fleur | 156/154 |
| 4,115,182 | 9/1978 | Wildmoser | 156/515 |
| 4,205,221 | 5/1980 | Meyer | 219/230 |
| 4,317,986 | 3/1982 | Sullivan | 219/231 |
| 4,430,069 | 2/1984 | Carlisle | 493/203 |
| 4,529,472 | 7/1985 | Hsu | 156/498 |
| 4,551,965 | 11/1985 | Prottengeier | 53/463 |
| 4,693,058 | 9/1987 | Kovacs | 53/552 |
| 4,752,204 | 6/1988 | Kataoka | 219/243 X |
| 4,768,326 | 9/1988 | Kovacs | 53/374.8 |
| 4,952,777 | 8/1990 | Kogasaka | 219/243 |
| 4,967,059 | 10/1990 | Wagner | 219/230 |
| 5,107,095 | 4/1992 | Derbyshire | 219/230 |

Primary Examiner—David A. Simmons
Assistant Examiner—J. Sells
Attorney, Agent, or Firm—Roylance, Abrams, Berdo & Goodman

[57] ABSTRACT

A machine for making bags or pouches for transporting animal organs for transplantation. The invention machine is small and light weight, and completely sterilizable for use in this environment. The invention also includes additional features of a special corona treatment for the films forming the laminates from which the pouches are made, and heat seals added to the finished pouches to facilitate tearing open of the pouch in a proper manner even in the event of delamination of one of the films.

5 Claims, 5 Drawing Sheets

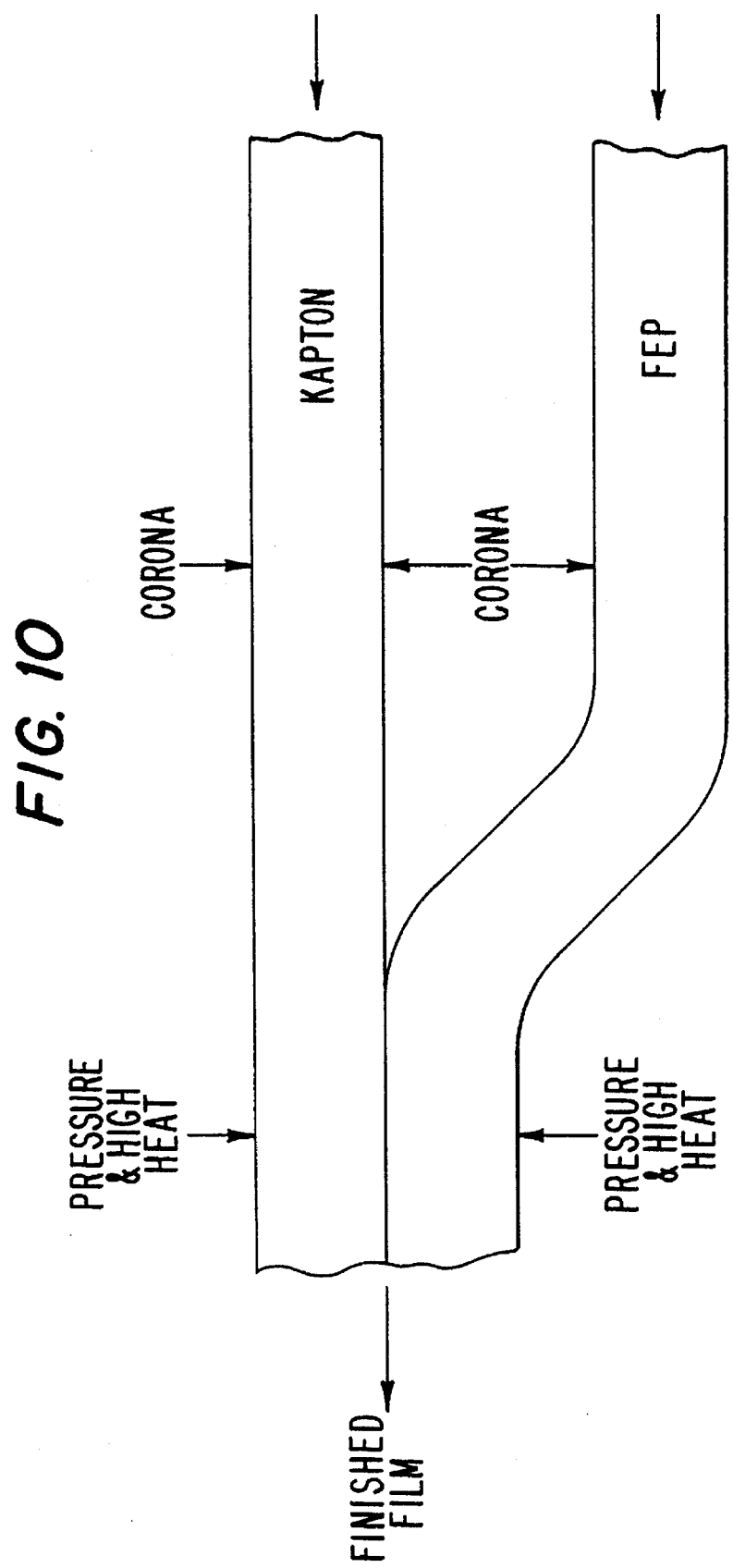

PEEL PACKAGE SEALING MACHINE

REFERENCE TO RELATED APPLICATION

This application is a continuation-in-part of my U.S. patent application Ser. No. 07/929,205 filed Aug. 14, 1992 U.S. Pat. No. 5,253,754.

FIELD OF THE INVENTION

The present invention relates to peel pouches as used in the packaging of medical devices, equipment, and transplant organs. More particularly, the invention relates to a peel pouch which can be subjected to liquid nitrogen temperatures without becoming brittle. The invention further relates to a heat sealer to be used with these pouches.

BACKGROUND OF THE INVENTION

Packages and particularly pouches having a peelable seal are well known in the medical field for containing sterile equipment. A peel pouch is an envelope or pouch often times constructed by welding two films together around three sides leaving one end open. An object is then placed inside the pouch, and the pouch then sealed on the fourth side. The pouch usually has an end with generous flaps which may be held in the hands and pulled apart. When this is done, the pouch peels open, revealing its contents in a manner such that they may be removed without any additional contact with the exterior surfaces of the pouch. This peel characteristic is accomplished by using a special adhesive to bond the films together, such that the adhesive strength is lower than the tear strength of the films.

In the medical and biotechnology fields, there are many uses for peel pouches. When an operator opens the pouch by peeling the layers apart, the contents of the pouch can be withdrawn from the pouch without violating sterility. In contrast, a simple bag must be cut open with a scissors or knife which can carry contamination into the interior of the bag or damage the contents.

The peeling process is typically facilitated by the use of a chevron shaped seal at one end. The seal is formed by heat sealing in the shape of a "v" whose apex points outward from the interior of the pouch. Peel tabs formed from excess lengths of the back and the front films extend outward from the pouch past the chevron seal. When the operator pulls on the peel tabs, the tearing of the adhesive is started by the apex of the chevron. In addition to the use of a chevron and peel tabs, the adhesive seal must have a peel strength below the tensile strength of the films which comprise the front and back of the pouch, so that during peeling the adhesive fails but the films do not tear.

Many peel pouches consist of a clear film on one side and a paper layer on the other side. This allows visual examination of the contents while they are still in the pouch, while the paper allows penetration of gas or steam for the sterilization of the contents. The clear film is usually a dual layer film such as polyester bonded to polypropylene. The polypropylene serves as a hot melt adhesive which allows the film to be bonded to the paper backing. Upon peeling, the polypropylene delaminates a thin layer from the surface of the paper, allowing a controlled strength peel.

In the organ transplantation field, an outer pouch frequently consists of a metal foil-polyethylene laminate. This laminate has disadvantages in that it is not transparent and occasionally breaks during shipping at liquid nitrogen temperatures. In addition, the pouch is not peelable, and so has to be cut open with sterile scissors at the time of use. This creates the risk of contamination entering the interior of the pouch. The inner pouch is a nylon polyethylene laminate which is transparent, but is subject to embrittlement when frozen at liquid nitrogen temperatures.

Peel pouches heretofore have had the disadvantage of being produced from materials which are not stable at cryogenic temperatures and become extremely brittle at such storage temperatures. These pouches are therefore unsuitable for storing materials, such as biological tissue and cells, at cryogenic temperatures. Examples of this type of peel pouch are found in U.S. Pat. Nos. 4,358,015, 4,352,429, 4,190,154 and 4,121,714.

Packages are also known which can be used to store blood or other materials at cryogenic temperatures. These packages do not include peelable seals, thereby requiring the package to be cut by scissors or a knife, and risking contamination of the contents. An example of this type of package is disclosed in U.S. Pat. No. 3,942,529.

SUMMARY OF THE INVENTION

The package produced in accordance with the invention obviates the disadvantages and limitations of the previous packages while providing an effective package which can maintain the contents in a sterile condition. The present invention is directed to a package which can be easily heat sealed and provided with a peelable seal to reduce the risk of contamination of the sterile interior of the package.

It is therefore an object of the invention to produce a package which can be easily opened without the need for scissors, a knife or other tool to contaminate the package or its contents.

It is an object of the invention to provide an improved heat sealing machine which is simple in construction, and is built around a standard tool.

A further object is to provide such a heat sealing machine which is entirely detachable together with its heat shield from the remainder of the sealing machine of the invention, and which is separately sterilizable. Organ transplantation, the particular environment for which the invention has been developed, demands sterility in the interior of the package.

Yet another object of the invention is to provide certain other advantages in the art, including the provision of an improved method of assuring that this package will open properly, and including certain corona treatments of the films going into making the packages of the invention, to achieve certain other advantages for packages made in accordance with the invention.

It is a further object of the invention to produce a sterile package which remains flexible at cryogenic temperatures.

Another object of the invention is to produce a package that is sufficiently transparent to enable viewing of the contents at cryogenic temperatures.

Another object of the present invention is to provide a new and improved method and apparatus for the manufacture of a package, bag or the like for biomedical use, fabricated from laminated films having thicknesses on the order of 0.5 to 2 mils and preferably about 1 mil in which the welds are of maximum strength and the edges of the finished articles are smooth and free of burrs.

A further object of the invention is to provide a new and improved process and apparatus for manufacturing animal organ bags in which the bags can be large and strong, yet dies are not required for their manufacture, and the process is simple and economical.

The above objects of the invention are basically attained by producing a peelable package comprising a first laminate layer including an inner layer of fluorinated ethylene propylene copolymer and an outer layer of a thermosetting polyimide; a second laminate layer heat welded to said first layer to define a continuous peelable seal and closed inner cavity, the second laminate layer including an inner layer of a fluorinated ethylenepropylene copolymer and an outer layer of a thermosetting polyimide having a decomposition temperature higher than the melting temperature of said inner layer; the inner layer of the first laminate layer being heat sealed to the inner layer of the second layer to define said peelable seal; the inner layers of the first and second laminates each having a thickness such that the inner layers have a tear strength less than the bond strength between the inner and outer laminated layers.

Other objects of the invention are basically attained by a machine for and a method of packaging a transplantable animal organ in a peelable package, the method comprising superimposing first and second laminate layers including an inner layer of fluorinated ethylene propylene copolymer and an outer layer of a thermosetting polyimide, the first and second laminate layers being superimposed with the inner layers facing one another; heat sealing the first and second laminate layers together to form first and second spaced apart side seams and a first end seam extending between said side seams to form an open-ended cavity; placing a transplantable animal organ in the open-ended cavity; and heat sealing a second end seam extending between said side seams to define a closed cavity containing said organ; the inner layers of the first and second laminate layers having a thickness such that the inner layers have a tear strength less than the bond strength between the inner and outer laminated layers.

BRIEF DESCRIPTION OF THE DRAWINGS

The advantages and description of the invention are discussed in conjunction with the drawings also forming a part of this disclosure and in which:

FIG. 10 is a schematic view showing the manner of making laminated films using selective corona treatments, in accordance with the invention.

DETAILED DESCRIPTION OF THE INVENTION

The present invention is directed to a pouch or package having a peelable seal and to a method and heat sealing apparatus for producing the pouch. The invention is further directed to a method of storing an organ for transplantation using the novel pouch of the invention.

In the field of organ transplants the packages and pouches used in transporting the organ must satisfy several requirements. The pouches for use in organ transplantation must maintain sterile conditions, be able to transport the organ safely at liquid nitrogen temperatures, and be opened easily at the site without contaminated instruments contacting the organ.

The pouch should be sufficiently transparent to allow examination of the organ prior to opening the pouch. The organs are usually double sealed in a first bag within a second bag and frozen in liquid nitrogen. The organ may be sealed while immersed in a cryoprotectant (freezing fluid) which typically contains DMSO, a very aggressive chemical. The inner surface of the pouch must be noncontaminating, inert, and harmless to living human cells. The bag further must be able to withstand the low temperatures at liquid nitrogen temperatures without becoming brittle or weak.

The pouch must arrive clean at the organ bank where the organs are inserted into the pouch. The pouch must also be resistant to the rigors of sterilization without losing its physical or chemical properties or absorbing the sterilizing gas. An opening for the organ must be provided, or an easy and sterile means for opening the pouch must be provided. The opening must be sealable under sterile conditions at the transplant service center by use of reasonably simple machinery and procedures. The invention includes such a heat sealing machine. The outer surface of the pouch must be able to accept ink for labeling and for writing on the pouch at the time of organ insertion.

The machine, pouch and method of packaging organs in accordance with the invention satisfies all of the requirements for transporting organs. The pouch is transparent to allow inspection of the organ before opening, easily sterilized without destroying the properties of the pouch, and able to withstand storage at temperatures of liquid nitrogen.

Figure 1:
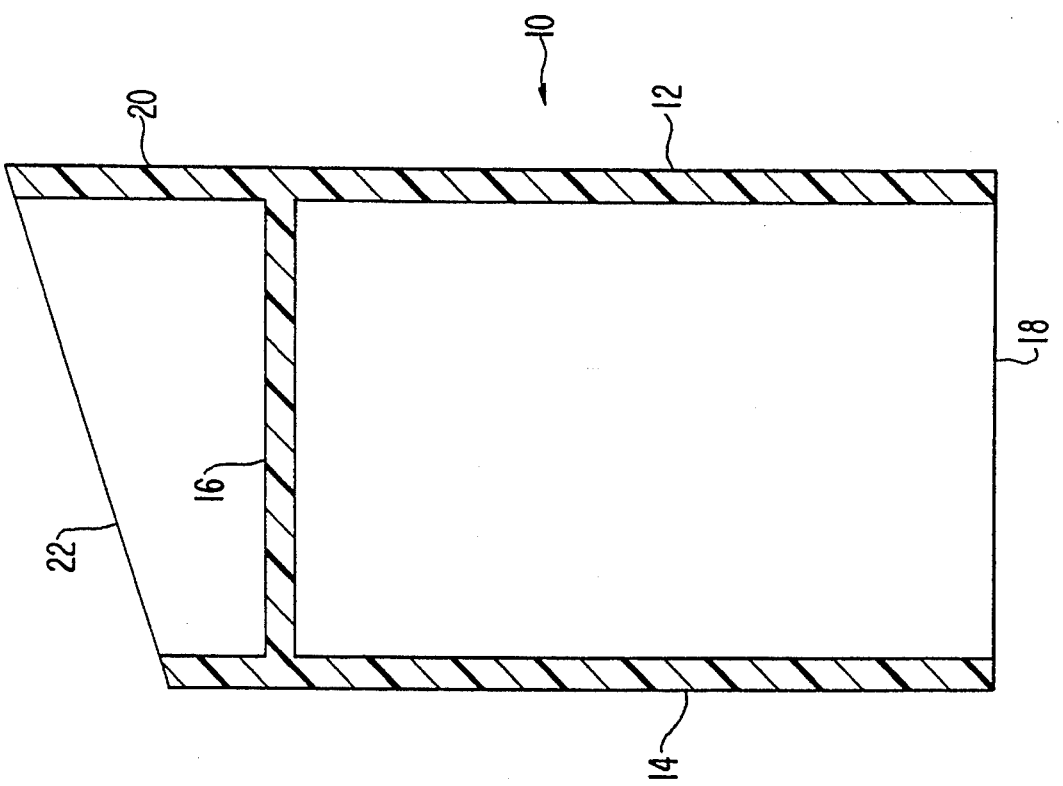
FIG. 1 is top plan view of a first embodiment of the pouch in accordance with the invention.

Referring to FIG. 1, the pouch 10 for storing and transporting animal organs and in particular human organs is formed from a two-layer laminate. Two sheets of the laminate are placed together and heat sealed along the edges to form side seams 12, 14 and along at least one end to form an end seam 16. As shown in FIG. 1, the pouch is initially formed with an open end 18.

In preferred embodiments, one of the side seams 12 extends beyond the end seam 16 to form a leg 20 and triangular shaped tabs 22. The tabs 22 enable the user to easily grip each of the sheets and pull the sheets apart to open the pouch as discussed hereinafter in greater detail. Optionally, the side seam 14 may extend to the end of tabs 22, as shown in FIGS. 1–3 and 6, or may end at end seam 16, see FIG. 4.

The laminate which is used to form the pouch includes an inner layer of a material which is chemically inert to the organ. A material that is particularly desirable is a fluorinated ethylenepropylene copolymer, such as tetrafluoethylene-hexafluoropropylene copolymer. A suitable material for use in producing the pouch is produced by E. I. DuPont under the tradename Teflon-FEP. This inner layer of fluorinated ethylenepropylene copolymer has a relatively low strength and must be reinforced by an outer layer of durable material to resist wear and rupture during use. A particularly suitable material for the outer wear layer is a non-thermoplastic polyimide such as that produced by E. I. DuPont and sold under the name Kapton. The material is sold as a laminate having a layer of fluorinated ethylenepropylene copolymer bonded to a layer of a polyimide. One such laminate is sold under the name Kapton-Type FN by Dupont.

In alternative embodiments, the laminate may have a greater number of layers. The inner layer should, however, be a fluorinated ethylene propylene copolymer.

The above described laminate is particularly desirable for producing pouches for transporting and packaging organs since the material is able to withstand freezing at the low temperatures of liquid nitrogen. In addition, the laminate is able to withstand sterilization temperatures by heating to as high as 200° C. The laminate and the resulting pouch may be used in a very broad temperature range from freezing at cryogenic temperatures to sterilizing temperatures.

The outer layer of the laminate preferably has a decomposition point higher than the inner. In preferred embodiments, the outer layer is able to withstand temperatures up to about 400° C. without delaminating from the inner layer. The inner layer preferably has a melting point range of about 300° C. such that the inner layer can be heat welded to the inner layer of an adjacent film.

The laminate of a polyimide and fluorinated ethylenepropylene copolymer provide a heat sealable pouch that is impervious to dimethylsulfoxide (DMSO) and is compatible with living cells. The outer polyimide layer is sufficiently strong to provide a wear resistant layer and to provide sufficient strength for peeling the package open.

In embodiments of the invention, the layers of the laminate are relatively thin, generally in the range of 0.5 to 2 mils (12 to 50 microns) each, preferably about 0.5 to 1 mil each. In a preferred embodiment of the invention, each layer of the laminate is about 1 mil. The use of thin films reduces the strain on the package when frozen, and thus, reduces the tendency to crack when frozen. Thin layers further provide for the necessary transparency of the pouch. The polyimide has a natural brown color which can make the pouch opaque if the film is too thick.

The thickness of the films is important in providing the peel characteristics of the finished pouch. The films must be sufficiently thick to provide the required strength to the pouch. The inner layer of fluorinated ethylenepropylene copolymer must be sufficiently thin so that the inner layer easily tears during opening. Conversely, the outer polyimide layer must be sufficiently thick to provide the strength to ensure the outer layer will not tear during opening.

In preferred embodiments, the inner and outer layers are substantially the same thickness. In alternative embodiments the films may be of different thicknesses provided the inner layer is sufficiently thin to tear during opening. In preferred embodiments, the thickness of the outer polyimide film is equal to or greater than the thickness of the inner layers.

Also important to the strength of the pouch and the peel characteristics of the seal is the bond strength between the layers of the laminate. The bond strength between the layers of the laminate is selected so that when the two sheets of laminate are peeled apart, at least one of the inner layers, along the seam, delaminates from the outer layer and tears along the seam. If the bond strength between the layers of the laminate is too weak, the entire outer layer will delaminate leaving behind a skin of the inner layer on the opposing laminate thereby still enclosing the organ in the pouch. A bond between the inner and outer layers which is too strong will not delaminate easily during opening thus forcing the laminate or the welded seal to tear when opening the pouch.

The bond strength between the inner fluorinated ethylene propylene copolymer and the outer polyimide layer may be controlled by various treatments during the manufacturing of the laminate. For example, the polyimide layer may be subjected to a corona discharge treatment before laminating to the fluorinated ethylenepropylene copolymer. In addition, the laminate may be baked after the fluorinated ethylenepropylene copolymer is laminated to the polyimide to enhance adhesion.

The fluorinated ethylenepropylene copolymer film in preferred embodiments is subjected to corona discharge treatment only on the side adjacent the polyimide layer to maintain sterility of the side forming the inner surface of the pouch. In many laminates, the manufacturer subjects the fluorinated ethylenepropylene film to a corona discharge treatment on both sides. It is important to maintain the surfaces of the laminates contacting the organ in as pure a state as possible. These corona treatments are described in greater detail below with reference to FIG. 10.

The pouch 10 is produced by overlaying two sheets of the laminate with the fluorinated ethylenepropylene layers contacting each other. The laminates are pressed by the heat sealing machine of the invention which includes a heated bar as described below to apply heat through the outer layers to melt the inner layers together without melting the outer layers. The heat is applied for a sufficient length of time to completely fuse the inner layers together under the heated bar and form seals 12, 14 and 16. As shown in FIG. 1, a side seam 20 is formed which extends from the body of the pouch. A substantially triangular shaped flap 22 of the laminates extends from the seals 16 and 20.

Figure 2:
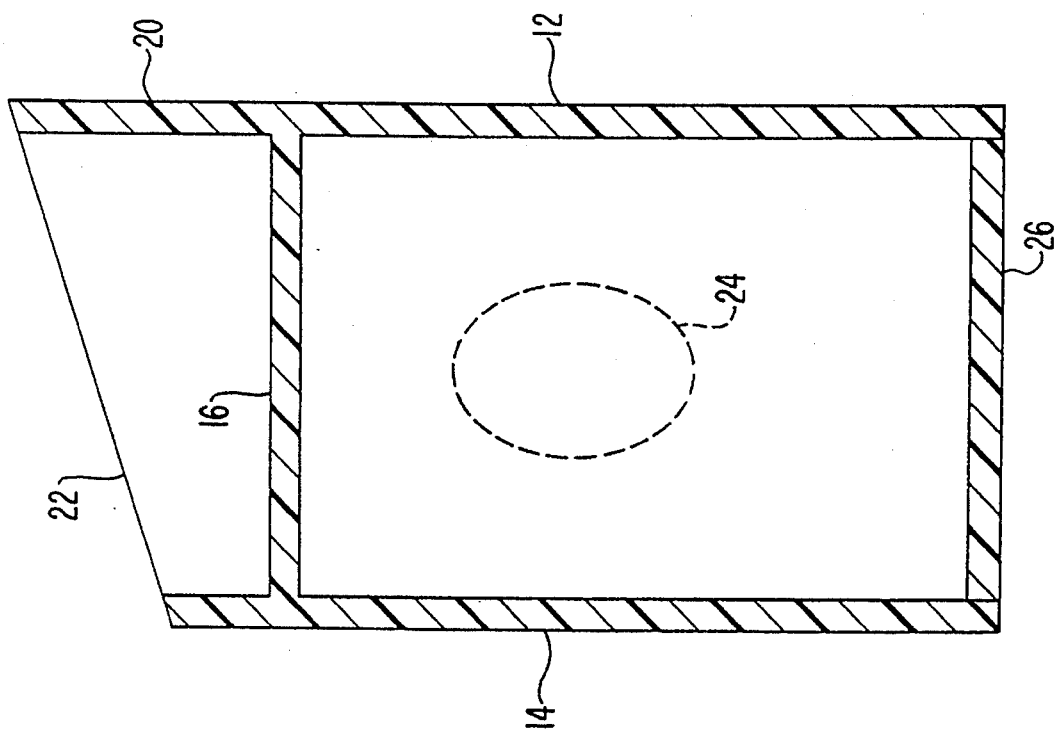
FIG. 2 is top plan view of pouch of FIG. 1 containing an animal organ and being heat sealed.

In use, an organ 24 shown in phantom lines of FIG. 2 is inserted through the open end 18 of the pouch 10. A bottom seal 26 is formed by applying heat to fuse the inner layers together, again using the machine of the invention. The pouch may then be frozen and shipped to the desired destination.

Prior to use, the pouch is sterilized by conventional practices. In addition, suitable indicia, a logo, etc., may be applied to the outer surface by conventional silk screening techniques, hand writing, or the like.

Figure 5:
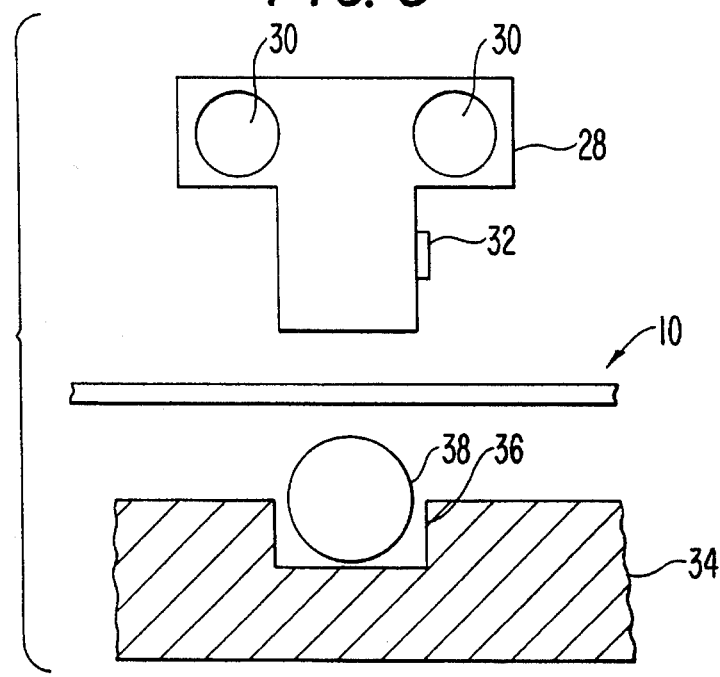
FIG. 5 is a side view of the heat sealing apparatus in accordance with the invention.

The sealing machine of the invention in a preferred embodiment is illustrated somewhat conceptually in FIG. 5, and in greater detail in subsequent Figures. The device includes a temperature controlled bar 28. Heating elements 30 are provided in the bar to heat the device. A thermocouple 32 is used to maintain the desired temperature. Control means, not shown, are detachably connected to thermocouple 32 and heating elements 30. The bar 28 is mounted for reciprocating motion, in a manner described in detail below, to press the sheets between the bar 28 and a platen 34. The platen 34 includes a groove 36. A silicone rubber cord 38 is positioned in the groove 36 to press the sheets of the laminate against the bar 28.

Chevron peel seals as are known in the art have been found difficult to make using the laminated sheets of the invention. Thus, one end of the pouch is extended as shown in FIG. 1. The end is trimmed to leave a sharp pointed corner. The pointed corner will start a tear in the inner layer of the laminate and propagate along the seam as the sheets are pulled apart. In alternative embodiments, the pouch may include a chevron shaped seal.

Figure 3:
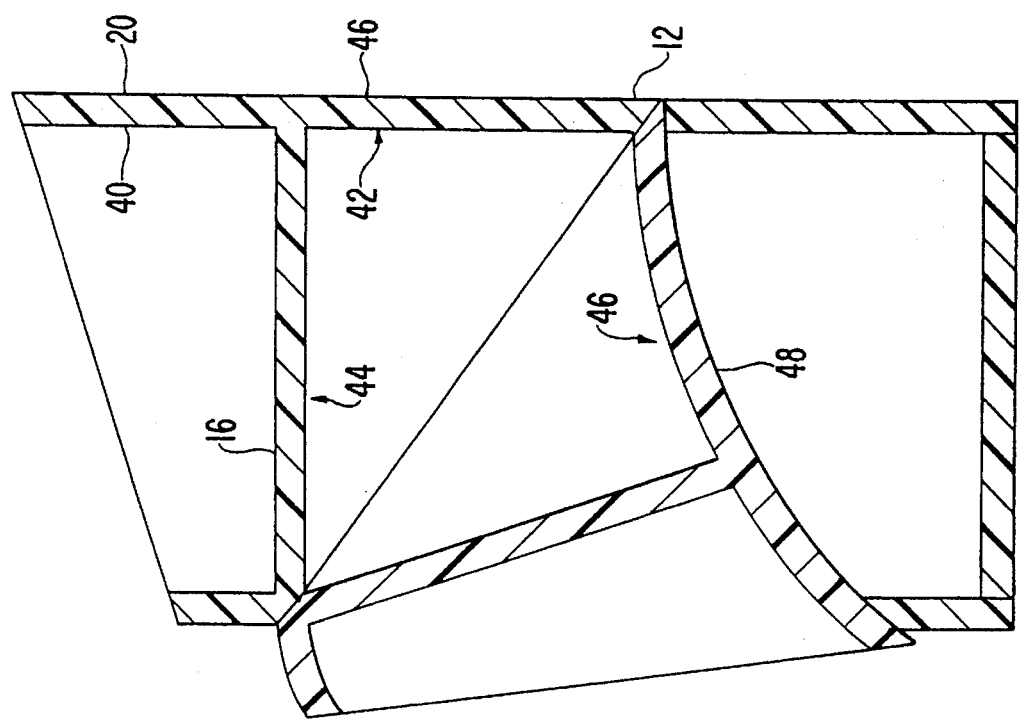
FIG. 3 is perspective view of the pouch of FIG. 2 in the partially open state.

During opening of the pouch 10 as shown in FIG. 3, the seal 20 will start to tear along the inner edge 40 and propagate to the inner edge 42 of side seal 12 and the inner edge 44 of the end seal 16. Also, the inner layer 46 of the laminate and the welded seal 48 of the fluorinated copolymer layers between the laminates separates from the outer layer to expose the polyimide layer 46.

Figure 4:
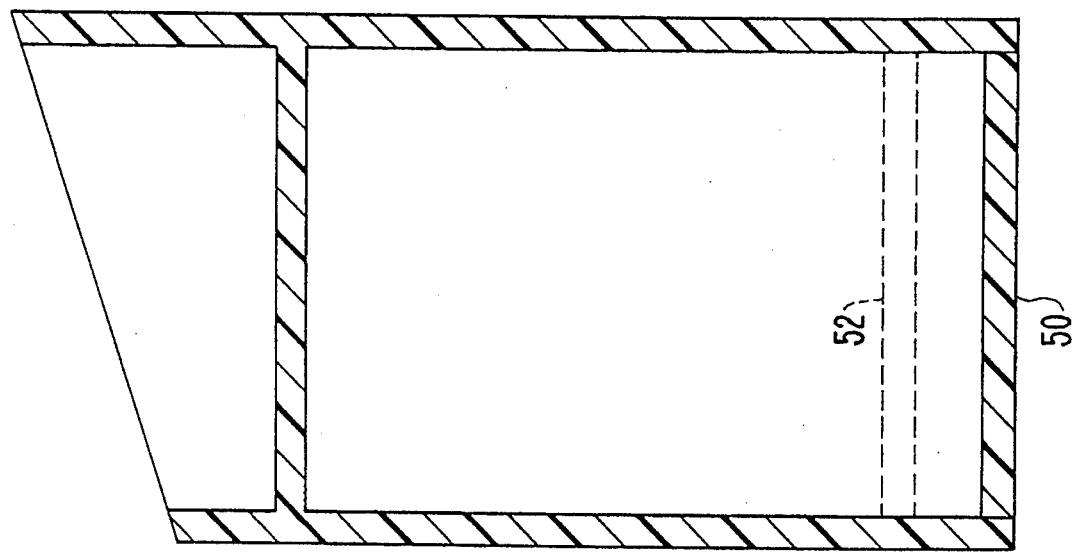
FIG. 4 is a top plan view of a second embodiment of the pouch of the invention.

In an alternative preferred embodiment, the pouch is produced having four sealed edges as illustrated in FIG. 4. The interior of the completely sealed pouch is thus easily maintained in a clean condition. Subsequent handling of the pouch, such as for silk screening, will not contaminate the interior of the pouch. The pouch thus arrives at the site in a completely clean condition.

In use, the operator cuts one of the end seals from the pouch, such as end seal 50 as shown in FIG. 4, to produce an open ended pouch similar to that illustrated in FIG. 1. The pouch may then be sterilized as needed before the organ to be transported is placed in the pouch. A second end seam 52 as shown in phantom lines of FIG. 4 is then formed by heating the laminates as before between the platen and the heated bar. The pouch is completely sealed to enclose the organ so that the pouch can be labeled and shipped. The sealed pouch is then frozen over liquid nitrogen and transported to the desired destination. The pouch is then opened by peeling the sheets apart so the organ can be removed.

In a further embodiment, the pouch is produced by sealing all of the edges as discussed above to form a closed pouch. When the pouch is ready for use, one of the end seals is peeled open instead of being cut. By peeling the pouch open, the risk of contamination of the interior of the pouch is reduced. The organ is then placed in the pouch and a new heat seal is formed as above to again close the pouch. The pouch is then frozen and transported.

The pouch is able to receive the organ without any additional preparation. In practice, however, the organ is generally packaged with a cryoprotectant, which often contains DMSO. The organ may further be placed in an inner pouch or package before packaging in the peelable pouch of the invention, if desired.

Figure 6:
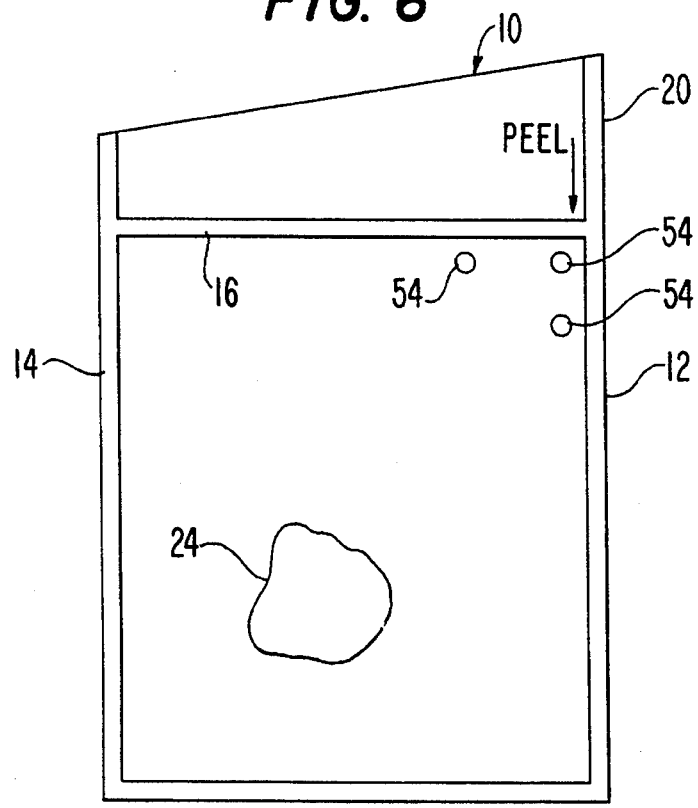
FIG. 6 is a view similar to FIG. 2 showing a modified version of the sealed pouch according to the invention.

FIG. 6 illustrates a variation of the pouch of FIG. 2 wherein a problem which occurs occasionally has been solved.

The problem is that when peeling the pouch apart, the operator grasps the films of the pouch in line with the word "PEEL" in FIG. 6, and begins opening the pouch from the open edge which is unsealed, as described above. The occasional problem is that the Teflon film sometimes only delaminates or separates from the Kapton film, and does not also tear at the seam 20. When this occurs, the organ 24 inside the pouch will remain covered by a thin Teflon membrane, in effect, remaining sealed inside the pouch. This then requires cutting using an implement, which is disadvantageous as set forth above.

The solution to this problem provided by this part of the invention involves the three small areas 54. These are sealed areas which may be simply created, as by a blunt tipped soldering iron and a thin silicone rubber pad. These spots 54 are created by relatively high pressure, which is inherent due to the small size of the spots 54. Also, a relatively high temperature is used, on the order of 375° C. The spots 54 can be made by hand or with a suitable apparatus.

When peeling the bag, the spots 54 will tear, because of the increased Kapton-Teflon adhesion created between the layers of the films. Also, the small circular shape of the spots 54 create strain points. Thus, tearing will occur at the spots 54, assuring that the Teflon will tear, and once the Teflon begins to tear it will continue to tear, thus eliminating the delamination and Teflon film enclosure problem of the organ as set forth above.

The heat seal spots 54 will not interfere with normal opening of the pouch. It is thought that the breaking will occur between the two facing FEP films on the inside of the pouch. Thus, the spots 54 solve a problem when it occasionally occurs, but do not create any new problems of their own when the pouch opens normally.

Figure 7:
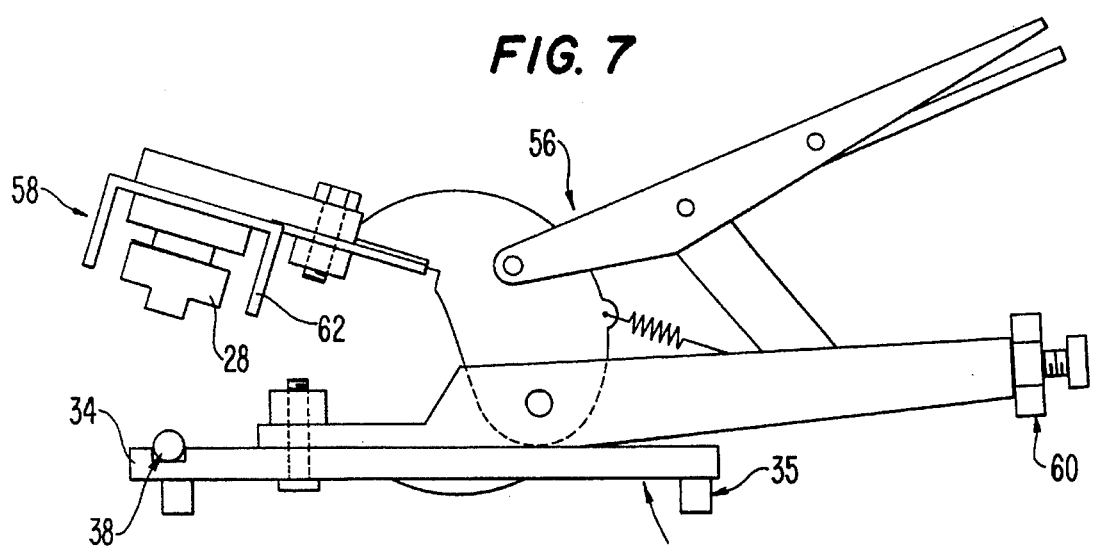
FIG. 7 is an end elevational of the heat sealer of the invention with the jaws open.
Figure 8:
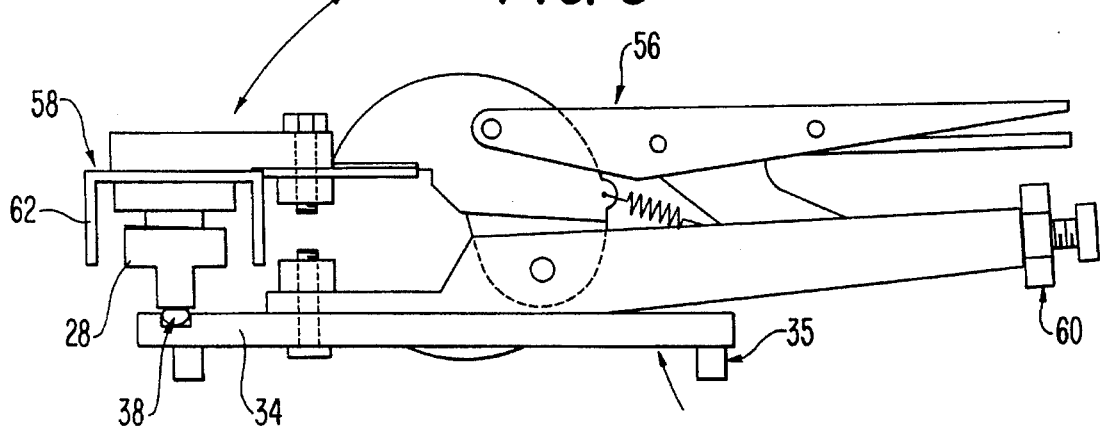
FIG. 8 is a view similar to FIG. 7 showing the jaws closed.
Figure 9:
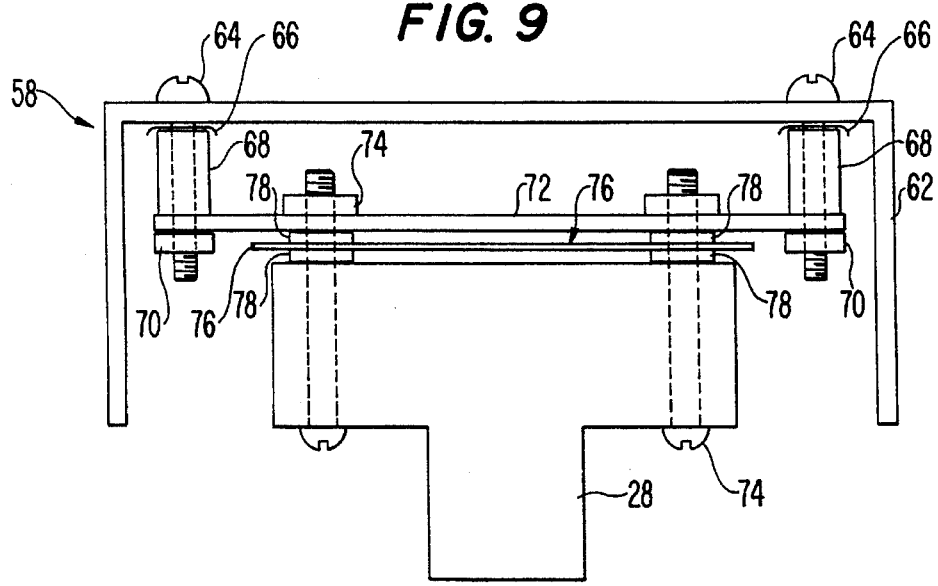
FIG. 9 is an enlarged side elevational view showing the manner of mounting the heating element in the heat shield and the heat shielding arrangement.

Referring now to FIGS. 7, 8 and 9, the heat sealing machine of the invention is shown in more detail.

The invention heat sealer comprises a modified but otherwise standard pair of VISE GRIP (registered trademark) pliers 56. The upper moving jaw of VISE GRIP pliers 56 is modified to carry the heating head 58. The lower stationary jaw carries the platen 34 in which is mounted the silicone cord 38.

Silicone rubber is available in many different colors. It has been found to be advantageous to use a bright color, red in particular, thus making it easy for the operator to see the cord as compared to the metal color of the platen 34.

An important advantage of this part of the invention is that by simply disconnecting the electrical leads, the entire apparatus shown in FIGS. 7 and 8 can be detached from the rest of the machine, which is primarily control apparatus not shown, and then separately sterilized. This is an important advantage of the invention, that is, its portability and ease of being sterilized, as compared to other heat sealers, for the organ transplant environment.

It can be seen that the heated bar 28 is above the silicone cord 38. Intuitively, one might expect that it would be easier to have the much simpler lower jaw carrying the platen 34 and the cord 38 only be the moving part. This platen 34, if desired, may be fitted with feet 35. The reason for the arrangement shown is that because of the relatively large amount of heat generated which the invention requires for sealing the pouches of the invention, if the heated jaw were below the work, the excess heat would flow up into the work, and make it much more difficult to control the seal. This is one of the primary reasons for the arrangement as shown. Another reason to have the upper jaw with the head 58 thereon be the moving part, is that it is easier to position the work, the pouch to be sealed, against a stationary silicone cord 38, rather than have this cord move after the work is positioned thereon.

Another modification of the VISE GRIP pliers 56 is the addition of the lock nut 60 on the adjusting screw of the pliers. Once the VISE GRIP pliers are set for a particular bag, temperature, particular films, particular silicone cord, and the like for a particular run of pouches to be made, the lock nut 60 is positioned thus assuring that the jaws will no longer move with respect to each other when they are in the closed position of FIG. 8. This assures repeated and consistent use in producing seals for that run. That is, any number of the same bags or pouches will be produced with no changes in the clamping pressure which produces the seals.

In this regard, the cord 38, shown without a pouch in place for clarity, is shown compressed in FIG. 8 as compared to FIG. 7. In typical applications of the invention to date, this compression has been adjusted such that the seals produced, that is the seals 12 and 14 of FIG. 2 for example, will be on the order of three sixteenths of an inch wide. Further, in regard to operating parameters, typical temperatures are usually in the range of 335° C. to 350° C. The dwell time of the bar 28 on the films to create these seals is 10 seconds minimum, and longer times can be used.

In order to control the substantial amount of heat involved, the head 58 includes an arrangement of heat shields to protect the user and keep the heat confined to the area of the bar 28 and the work, see FIG. 9. In addition to shielding against the heat, the head 58 must be designed so that relatively large forces are transmitted from the jaw and operating levers of the pliers 56 through the head 58 and to the work. This transfer of relatively high forces must occur without distortion of the bar 28 or the platen 34.

Overall, the objectives of the heater head shielding is to establish a long relatively low thermal conductivity path in the smallest possible space. This is to assure that a minimum amount of heat is transferred from the heater block 28 to the outer frame 62. At the same time, this needs to be done in such a way as to keep the apparatus small and of light weight.

The outer shield 62 is connected via screws 64, heat breaks 66, sleeves 68 and nuts 70 to a relatively strong main stainless steel plate 72. Four such sets of the parts 64 to 70 may be provided. The screws 64 and nuts 70 hold the apparatus assembled, but are not involved in transmitting the thrust or sealing forces from the frame 62 to the bar 28. As shown in FIGS. 7 and 8, the upper jaw of pliers 56 is connected to frame 62 by suitable fasteners. A pair of screw and nut assemblies 74 at each end of bar 28 join the heated bar 28 to the main plate 72 with a relatively thin thermal isolation plate 76 trapped therebetween by washers 78. Radiant heating of the main plate 72 is reduced by the shield 76. The shield 76 is preferably formed of aluminum because it is a good heat reflector and is of low cost and readily available. The washers 78 are preferably split springy stainless steel washers. They will thus not only insulate against heat, stainless steel having a low thermal conductivity, but will also hold the apparatus together, even if one assembly 74 is released.

For heat to conduct from the heater block 28 to the outer frame 62, it must pass through the washers 78 and then to the main stainless steel plate 72. Stainless steel is known for its low thermal conductivity and high strength, both of which characteristics are highly desirable in the head 58 of the invention. The heat must then reach the stainless steel spacers 68 and must then pass through the tapes 66. These tapes are preferably formed of Kapton which provide a layer of extraordinarily low thermal conductivity, and thus serve as thermal breaks. The screws 64 and 74 provide an undesirable additional thermal path, but since the screws are made of stainless steel, and thus are of low thermal conductivity, and since they are smaller in cross section than the washers 78 and the spacers 68, these screws thus contribute to the total heat flow only to a minor extent. It has been found that even with the relatively high temperatures used, the outer frame 62 is covered with plastic so that it is not overly dangerous to the operator.

The length of the bar 28 and the shield 62 is on the order of 6 to 10 inches in the successfully constructed embodiments. This dimension will depend upon the length of the elongated seals required for the pouch to be made in accordance with the invention. This length is not visible in FIGS. 7–9, it is the dimension which extends into the plane of the paper.

The invention heat sealing machine comprises the device shown in FIGS. 7–9, together with means for controlling the heater 30 and thermocouple 32 in the device. This part of the invention heat sealer is not shown. The two parts, the sealing head and the controller, are connected together by two electrical wires and plugs which are easily disconnectible from the heating head shown in FIGS. 7–9. After being disconnected, the entire apparatus of the pliers 56 with the head 58 on one jaw and the platen 38 on the other becomes easily portable and readily sterilizable, as is needed for the organ transplantation environment for which the invention was developed.

Another aspect of the invention is the corona treatments of the layers that go into the making of the films. FIG. 10 shows the Kapton and FEP layers being brought together using state-of-the-art pressure rollers and heat applying means to create the finished film.

By way of background, a corona treatment is one in which plastic film is rendered more bondable and more wettable. Wettability is important because, in use, information is written or printed on the outside of the bag. Bondability of the films is important, of course, in order to have the individual films bond together properly to form the layered films from which the pouches according to the invention are made.

The invention uses state-of-the-art corona treatments. Equipment made by Corotec Corporation of Collinsville, Conn. and Tantec of Schaumburg, Ill., among others, can be used to perform such corona treatments. Basically, such treatments comprise exposing the film to high voltage fields which accomplish the necessary modification of the surfaces of the films.

The FEP film must be corona treated or it will not bond at all. However, according to the invention, the FEP film is treated only on the side which will be bonded to the Kapton. The Kapton is corona treated on both sides. The untreated side of the FEP film will be exposed to the organ inside the pouch. For this reason, it is desirable that the FEP not be rendered wettable at all. Corona treatment of the Kapton on both sides is done, on the inside, to enhance the bonding to the FEP, and on the outside to permit writing or printing of information and the like on the finished pouch.

The above description is intended to be exemplary of embodiments of the invention. It is to be understood that numerous alternative embodiments and variations can be made without departing from the spirit and scope of the invention.

I claim:

1. A hand held heat sealing machine for making cryogenic temperature stable peelable packages for storing and transporting transplantable organs at cryogenic temperatures from a pair of laminated films, each of said films including an inner layer of fluorinated ethylenepropylene copolymer and an outer layer of a thermosetting polyimide, said machine comprising a pair of pliers having an upper moving jaw, a stationary lower jaw and a toggle and spring locking mechanism which releasably locks the upper moving jaw in fixed closed positions, a heating head and a heat shield fixed to said upper moving jaw, said lower stationary jaw including a platen, said platen comprising a silicone cord, said heating head comprising a heated welding bar having a heat temperature range of 635°–665° F., and said pliers being adapted to compress said laminates therebetween to form elongated heat seals to thereby make said films into said packages.

2. The machine of claim 1, said platen including feet means.

3. The machine of claim 1, wherein said pliers include an adjusting screw and a lock nut on said adjusting screw affixed to said lower stationary jaw to set said jaws repetitiously in the same relative closed position.

4. The machine of claim 1, said portion of said machine comprising said pliers with said heating head and said platen thereon being readily portable and sterilizable.

5. The machine of claim 1, said heat shield comprising an outer shield, heat insulating and thrust transmitting means interconnecting said heating bar and said outer shield, said last mentioned means comprising a main plate member, first fastener means interconnecting said plate member to said outer shield, and second fastener means interconnecting said plate member to said heated bar.

* * * * *